United States Patent [19]

Albisser et al.

[11] 4,452,599
[45] Jun. 5, 1984

[54] METHOD OF DELIVERING MEDICAL LIQUID BY PERISTALTIC TUBE PUMP

[75] Inventors: Anthony M. Albisser; Warren S. Jackman, both of Toronto, Canada

[73] Assignee: The Hospital for Sick Children, Toronto, Canada

[21] Appl. No.: 314,930

[22] Filed: Oct. 26, 1981

[51] Int. Cl.³ ............................................. A61M 5/00
[52] U.S. Cl. ..................................... 604/49; 604/153; 417/477
[58] Field of Search .......... 128/214 F, 273, DIG. 12; 417/474–477; 138/110, 137; 604/49, 151–153

[56] References Cited

U.S. PATENT DOCUMENTS

| | | | |
|---|---|---|---|
| 320,888 | 6/1885 | Ruffel | 417/476 |
| 2,696,173 | 12/1954 | Jensen | 417/477 |
| 3,105,447 | 10/1963 | Ruppert | 417/477 |
| 3,781,142 | 12/1973 | Zweig | 417/477 |
| 3,875,970 | 4/1975 | Fitter | 417/477 |

Primary Examiner—Dalton L. Truluck
Attorney, Agent, or Firm—Rogers, Bereskin & Parr

[57] ABSTRACT

A tube assembly for a peristaltic pumping system is described. The assembly includes resilient inner and outer tubes of which the inner tube has a lumen along which liquid can be pumped by occluding the tube and causing the point of occlusion to progress along a length of the tube defining a pumping zone. The outer tube fits closely around the inner tube and extends over said zone. The tubes are free of attachment to one another over at least a substantial part of said zone so that the contacting surfaces of the respective tubes define an interface along which relative movement between the tubes can occur during pumping. The tubes are secured together at at least one point along their lengths. It has been found that abrasion of the innermost surfaces of the inner tube is minimized and that reduced contamination of the liquid being pumped and increased pump tube life can be expected as compared with conventional peristaltic pump tubes.

1 Claim, 3 Drawing Figures

METHOD OF DELIVERING MEDICAL LIQUID BY PERISTALTIC TUBE PUMP

This invention relates to a tube assembly for a peristaltic pumping system.

Peristaltic pumping systems are well known; an example of a miniature peristaltic pump for insulin infusion is disclosed in DIABETES CARE Volume 3, No. 2, March-April 1980, published by the American Diabetes Association Inc. Tubes used in such systems are conventionally plain elastomeric tubes. A roller or system of rollers occludes the tube in the pump and the point of occlusion is made to progress along the axis of the tube by the driving mechanism of the pump. Pumping action is caused by positive pressure created ahead of the moving point of occlusion and negative pressure behind it. This type of system has the advantage that the fluid being pumped comes into contact with only one material (the tubing), the quality and content of which can be carefully controlled so as to minimize the risk of contamination of the fluid.

In practice, it has been found that a serious disadvantage of conventional peristaltic pump tubes is wear. Particles from the inner surface of the elastomeric material from which the tube is made may become dislodged from the tube and contaminate the fluid being pumped. This is believed to be caused by relative motion occurring between opposing portions of the inner surface of the tube at the point of occlusion. This abrading motion causes particles of the elastomeric material to be dislodged into the stream of fluid being pumped. Particularly in devices such as heart-lung machines, this contamination has been identified as a problem of serious dimensions.

An object of the present invention is to provide improvements aimed at minimizing this abrasion problem.

According to the invention there is provided a tube assembly for a peristaltic pumping system. The assembly includes a resilient inner tube having a lumen along which fluid can be pumped by occluding the tube and causing the point of occlusion to progress along length of the tube defining a pumping zone. An outer resilient tube fits closely around the inner tube and extends over a length of the inner tube corresponding to the pumping zone. The tubes are free of attachment to one another over the length of the pumping zone so that the contacting surfaces of the respective tubes define an interface along which relative movement between the tubes can occur during pumping. The tubes are secured together externally of the pumping zone.

In practice, it has been found that this form of tube assembly minimizes the abrasion problem at the innermost surface because the relative wall motion caused by the action of the peristalic pump is made to occur mainly outside the pump tube lumen, i.e. at the interface between the two tubes. The opposed wall portions of the inner lumen are relieved of the shear stresses which would otherwise result in the abrading action which releases the undesirable particulate material into the lumen.

In order that the invention may be more clearly understood, reference will now be made to the accompanying drawings which illustrate a preferred embodiment to the invention by way of example, and in which.

Figure 1:
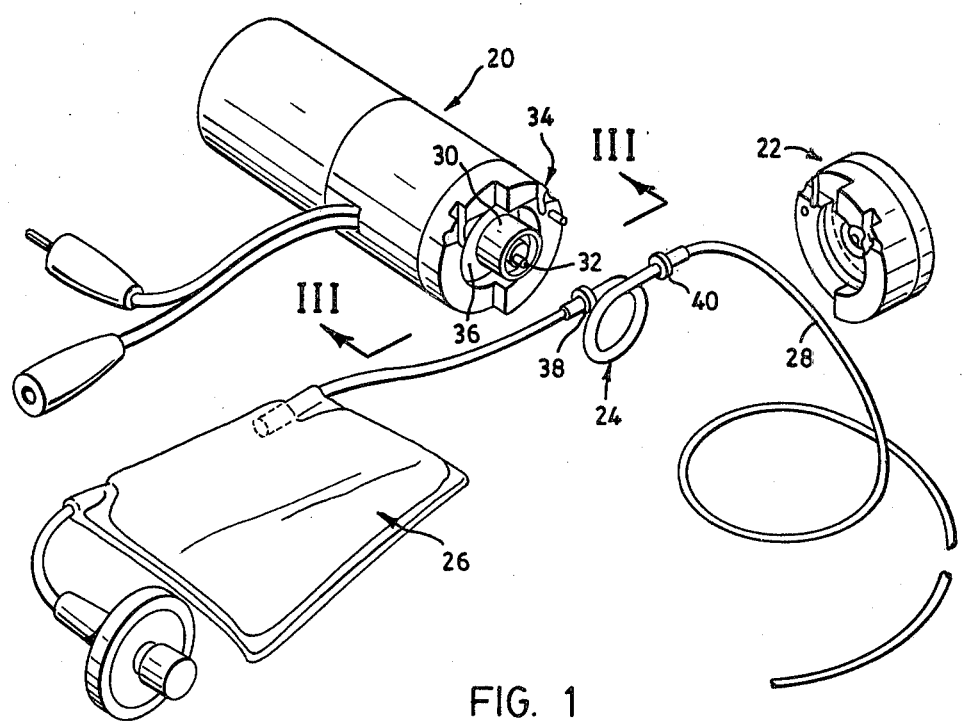
FIG. 1 is a perspective view of a tube assembly according to a preferred embodiment of the invention shown in exploded relationship with a conventional peristaltic pump.
Figure 3:
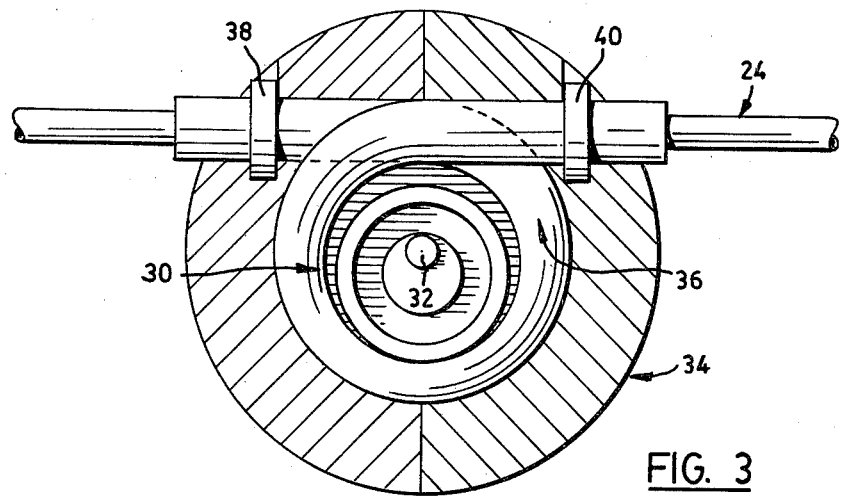
FIG. 3 is a sectional view on line III—III of FIG. 1 showing the tube assembly in position in the pump.

The peristaltic pump as shown in FIGS. 1 and 3 is generally of the form disclosed in the DIABETES CARE publication referred to above but in FIG. 1 is shown in association with a tube assembly of the form provided by the invention. The pump is generally denoted by reference 20 and includes a cover 22 shown removed as for installation of the tubing assembly. The tubing assembly itself is generally indicated at 24 and is shown connected to an insulin infusion reservoir 26 at one end and, at its opposite end, to a catheter tube 28.

The principal components of pump 20 are a cylindrical rotor 30 which is mounted on an eccentric cam 32 which in turn is mounted on a drive shaft driven by an electric motor within the casing of the device. The rotor is received in a chamber defined by a stator, part of which is defined by cover 22 and the remainder of which is formed by a stator part 34 carried by the main pump housing. The chamber receiving rotor 30 is indicated at 36. It will be seen that the chamber is generally of annular shape for receiving a loop formed in the tubing assembly 24. Collars 38 and 40 on the tubing assembly (see also FIG. 2) are received in corresponding recesses in the stator parts 22 and 34 and serve to locate the tubing in the pump.

FIG. 3 shows the tube assembly in position in the pump and it will be seen that the rotor is eccentrically positioned in the chamber 36 and serves to occlude the tube assembly to a point within chamber 36. As the eccentric cam rotates on the drive shaft, the point of occlusion will progress along the tube, thereby producing the pumping action referred to above.

Figure 2:
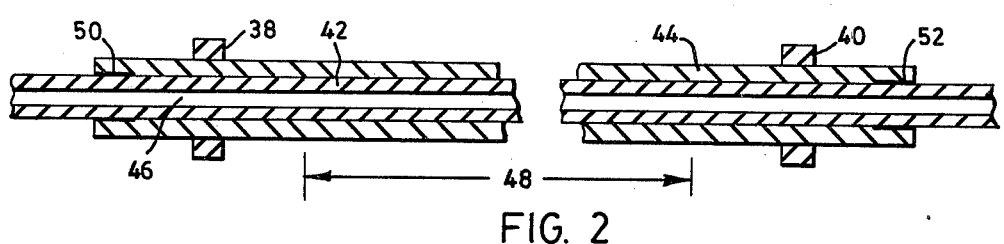
FIG. 2 is a longitudinal sectional view through the tube assembly shown in FIG. 1.

FIG. 2 shows the tube assembly 24 in section and it will be seen that the assembly comprises inner and outer tubes 42 and 44 respectively. Both tubes are resilient and in this embodiment are in fact made of Medical Grade Silicone Elastomer tubing made by Dow Corning Corp., Midland, MI, U.S.A. The inner tube 42 has a lumen 46 along which liquid can be pumped by occluding the tube as described above. The point of occlusion moves along a length of the tube defining a pumping zone; in this case, the zone is defined by the length of the tube which is within pumping chamber 36. Typically, the pumping zone might occupy a length of the tube assembly such as that indicated at 48 in FIG. 2. The outer tube 44 fits closely around the inner tube and extends over a length of the inner tube which includes the pumping zone 48. The nominal outside diameter of the inner tube 42 is chosen equal to the nominal inside diameter of the outer tube and the inner tube is drawn through the outer tube in forming the tube assembly. The assembly is made of sufficient length that the outer tube encloses the inner tube at least over the pumping zone 48 but in the illustrated embodiment, the outer tube projects beyond the active part of the tube, i.e. the part within the pump. The collars 38 and 40 referred to above are secured by adhesive to the outer tube at appropriate positions to be received in the corresponding recesses in the pump as discussed above.

The two tubes 42 and 44 are free of attachment to one another over the length of the pumping zone 48 so that the contacting surfaces of the respective tubes define an interface over which relative movement between the two tubes can occur during pumping. The tubes are secured together externally of the pumping zone. In this embodiment, the two tubes are secured together by adhesive in the area of end portions of the outer tube 44 only as indicated by reference 50 and 52 in FIG. 2. In an alternative embodiment, the tubes could be secured together in some other manner, for example, at one end of the outer tube only. The important criterion is that the tubes should be free of attachment to one another at least over the length of the pumping zone.

As explained above, the form of tube assembly provided by the invention has the advantage that the relative motion which normally occurs between opposed portions of the assembly during pumping can occur mainly at the interface between the two tubes, thereby at least partially relieving the opposed portions of the inner wall of the inner tube lumen of shear stresses which would otherwise result in an abrading action releasing undesirable particles of the tube material into the lumen of the inner tube. Natural lubricant (glycerine) which diffuses through the elastomeric material of the tubes reduces friction between the tubes at the interface and enhances the stress relieving effect of the tube design. Any wear particles generated by abrasion between the tubes are trapped and prevented from reaching the lumen along which flows the material being pumped. In addition, since the abrading surfaces are lubricated, increased pump tube life is to be expected.

It will of course be appreciated that the preceding description relates to a preferred embodiment of the invention and that many modifications are possible in addition to those referred to above. For example, the tubes could be secured together nearer the centre instead of at the ends of the outer tube. The particular materials referred to above are not to be considered as limiting and in fact it might be advantageous in some cases to make the tubes of different materials. Also, a thin layer of self-lubricating material could be incorporated between the two tubes. Another possibility is to add a third or even more additional tubes externally of the outer tube referred to above.

We claim:

1. A method of delivering a liquid medicament to a patient by means of a peristaltic pump, the method comprising the steps of:

providing a tube assembly which includes a resilient inner tube having a lumen along which liquid can be pumped by occluding the tube and causing the point of occlusion to progress along a length of the tube defining a pumping zone, and an outer resilient tube fitting closely around said inner tube and extending over a length of said inner tube which includes said pumping zone, said tubes being free of attachment to one another over at least the majority of the length of said zone while being secured together at at least one point along their lengths;

connecting said inner tube between a supply of said liquid and a patient;

occluding said inner tube at a point in said pumping zone by squeezing said outer tube, and repeatedly causing the point of occlusion to progress along said zone while permitting differential movement to take place between the tubes at said interface whereby particulate material released as a result of said movement is confined outside the lumen of the inner tube and contamination of said liquid flowing along the lumen is substantially avoided.

* * * * *